United States Patent [19]
Long et al.

[11] Patent Number: 6,022,703
[45] Date of Patent: Feb. 8, 2000

[54] EXPRESSION OF DNA SEQUENCES DERIVED FROM NOCARDIOFORM MICROORGANISMS

[75] Inventors: Susan Long, Wakefield; Gary R. Ostroff, Needham, both of Mass.

[73] Assignee: Genzyme Corporation, Cambridge, Mass.

[21] Appl. No.: 08/080,598

[22] Filed: Jun. 21, 1993

Related U.S. Application Data

[63] Continuation of application No. 07/914,048, Jul. 13, 1992, abandoned, which is a continuation of application No. 07/436,234, Nov. 14, 1989, abandoned, which is a continuation-in-part of application No. 07/269,669, Nov. 14, 1988, abandoned.

[51] Int. Cl.[7] .............................. C12P 21/06; C12P 21/04; C12N 15/53; C12N 15/76
[52] U.S. Cl. ...................... 435/69.1; 435/71.2; 435/190; 435/253.2; 435/252.35; 435/253.1; 435/320.1; 435/486; 536/23.2; 536/24.1; 536/23.7
[58] Field of Search .................... 435/69.1, 71.2, 435/91.1, 172.3, 190, 252.1, 253.1, 252.35, 320.1, 486, 253.2; 536/23.1, 24.1, 23.2, 23.7

[56] References Cited

U.S. PATENT DOCUMENTS

| | | | |
|---|---|---|---|
| 3,907,642 | 9/1975 | Richmond | 435/190 |
| 4,144,129 | 3/1979 | Gruber et al. | 435/190 |
| 4,745,056 | 5/1988 | Guterman et al. | 435/69.1 |
| 4,952,500 | 8/1990 | Finnerty et al. | 435/69.1 |
| 5,371,005 | 12/1994 | Fujishiro et al. | 435/190 |
| 5,602,017 | 2/1997 | Fujishiro et al. | 435/190 |

OTHER PUBLICATIONS

Cheetham et al., *Biochem.J.* (1982) 201, 515–521.
Ferreira et al., *Journal of Applied Bacteriology* 1984, 57, 429–446.
Aihara et al., *Journal of Applied Bacteriology* 1986 61, 269–274.
Lewin (1985) *Genes, Second Ed.* p. 185–196 & 205 John Wiley & Sons, Inc., N.Y.
*Bergey's Manual of Systematic Bacteriology*, vol. 4, Eds. Williams et al. p. 1458–1459. Williams & Wilkins, Baltimore 1989.
Murooka et al., 1986, Applied Environ. Microbiol., vol. 52 (6): 1382–1385.

*Primary Examiner*—David T. Fox
*Assistant Examiner*—Anne Marie Grünberg
*Attorney, Agent, or Firm*—F. Brad Salcedo

[57] ABSTRACT

A cloning vector contains a DNA sequence derived from a Nocardioform microorganism, and is capable of expressing the DNA sequence in a host microorganism. Recombinant cholesterol oxidase is produced by a host microbial cell transformed with a cloning vector containing cholesterol oxidase encoding DNA derived from a Nocardioform microorganism. A method for determining cholesterol oxidase in a sample of fluid from a human includes contacting the sample with the Nocardioform microorganism derived recombinant cholesterol oxidase.

21 Claims, 8 Drawing Sheets

```
         10         20         30         40         50         60
          *          *          *          *          *          *
GGGACTCCTG ATCTCAGCTT CCGTACTGGA GCGCGAAGCT CCTGCCCTGG CTGACGTAGT
CCCTGAGGAC TAGAGTCGAA GGCATGACCT CGCGCTTCGA GGACGGGACC GACTGCATCA 70         80         90        100        110        120
          *          *          *          *          *          *
TCTCACTCTT GTCTGATACC AACCTGTCTG ATACCCACCT GTTAGAACTC ACCGTAGTTC
AGAGTGAGAA CAGACTATGG TTGGACAGAC TATGGGTGGR CAATCTTGAG TGGCATCAAG 130        140
          *          *
TCGAACCCGA TGGAGTAGCC
AGCTTGGGCT ACCTCATCGG 150        160        170        180        190
          *          *          *          *          *          o
CGAAG ATG ACG GCA CAA GAC GAA AAG TTC CGA CTG TCC CGA CGA GGT TCC
      TAC TGC CGT GTT CTG CTT TTC AAG GCT GAC AGG GCT GCT CCR AGG
      Met Thr Ala Gln Asp Glu Lys Phe Arg Leu Ser Arg Arg Gly Phe
                                       AUTOTRANSLATION OF CO2
       o          o          o          o          o          o 200        210        220        230        240
          *          *          *          *          *          o
ATG GCC GCT GGA GCC GCC GGC GTG GCA GCG ACC GGA TTC GCC GGC TGG ACG
TAC CGG CGA CCT CGG CGG CCG CAC CGT CGC TGG CGT AAG CGG CCG ACC TGC
Met Ala Ala Gly Ala Gly Ala Val Ala Thr Ala Phe Ala Gly Trp Thr
                                       AUTOTRANSLATION OF CO2
       o          o          o          o          o          o
```

FIG. 2A

```
      250       260       270       280       290
       *         *         *         *         *
CCG GCC TAC GCC GTC CCC GCC GGC TCC TCC GGC GGT CCT
GGC CGG ATG CGG CAG GGG CGG CCG AGG CGC AGG GGT CCT
Pro Ala Tyr Ala Val Pro Ala Gly Ser Ser Gly Gly Pro
                  AUTOTRANSLATION OF CO2

300       310       320       330
       *         *         *         *
GTC TCC ACC CTC ACA CCG CCG CCC TTC CCC GAA GGC ATC GCG CTG
CAG AGG TGG GAG TGT GGC GGC GGG AAG GGG CTT CCG TAG CGC GAC
Val Ser Thr Leu Thr Pro Pro Pro Ala Phe Pro Glu Gly Ile Ala Leu
                  AUTOTRANSLATION OF CO2

340       350       360       370       380
 *         *         *         *         *
TAC CAG CAG GCA TAT CAG AAC TGG TCC AAA GAG ATC ATG CTC GAC GCG
ATG GTC GTC CGT ATA GTC TTG ACC AGG TTT CTC TAG TAC GAG CTG CGC
Tyr Gln Gln Ala Tyr Gln Asn Trp Ser Lys Glu Ile Met Leu Asp Ala
                  AUTOTRANSLATION OF CO2

390       400       410       420       430
 *         *         *         *         *
ATC TGG ACC TGT TCA CCC AAG ACG CCC GAA GAC GTA GTC GCC TCG CGA
TAG ACC TGG ACA AGT GGG TTC TGC GGG CTT CTG CAT CAG CGG AGC GCT
Ile Trp Thr Cys Ser Pro Lys Thr Pro Glu Asp Val Val Ala Ser Arg
                  AUTOTRANSLATION OF CO2
```

FIG. 2B

```
       440              450              460              470              480
        *                *                *                *                *
ACT GGG CCA TCC AAC GGC TAC ACC ATT CGT CCC CGG GGG CCA TGC GTG
TGA CCC GGT AGG TTG CCG ATG TGG TAA GCA GGG CCC GGT ACG CAC
Thr Gly Pro Ser Asn Gly Tyr Thr Ile Arg Pro Arg Gly Pro Cys Val
                      AUTOTRANSLATION OF CO2
       490              500              510              520              530
        *                *                *                *                *
GAC GCC GCT GAC CAT CGT CAA CGG TGC GCC GGT CGA CAA GGT CAT CCT
CTG CGG CGA CTG GTA GCA GTT GCC ACG CCA GCT GTT CCA GTA GGA
Asp His His Asp His Arg Gln Arg Cys Ala Gly Arg Gln Gly His Pro
                      AUTOTRANSLATION OF CO2
       540              550              560              570
        *                *                *                *
CGC CGA CAC CAC GGT CCA CCT CAC CGG CGT CTC CGT CAA CGC CGG TGG
GCG GCT GTG GTG CCA GGT GGA GTG GCC GCA GAG GCA GTT GCG GCC ACC
Arg Arg His His Gly Pro Pro His Arg Arg Leu Arg Gln Arg Arg Trp
                      AUTOTRANSLATION OF CO2
       580              590              600              610              620
        *                *                *                *                *
CAG CCC CGG CAC CGT CAC CGG AGG ACC CGG CGC GAC CCT CGA CGC CAT
GTC GGG CCG GTG GCA GTG GCC TCC TGG GCC GCG CTG GGA GCT CGG GTA
Gln Pro Gly His Arg His Arg Arg Thr Arg Arg Asp Pro Arg Arg His
                      AUTOTRANSLATION OF CO2
```

```
630         640         650         660         670
 *           *           *           *           *
CAC CAC CGC ACT GCA GGC ACA GGG CCT CGG GTT CGC GAA CTG CCG GCG
GTG GTG GCG TGA CGT CCG TGT CCC GGA GCC CAA GCG CTT GAC GGC CGC
His His Arg Thr Ala Gly Thr Gly Pro Arg Val Arg Glu Leu Pro His
                        AUTOTRANSLATION OF CO2

680         690         700         710         720
 *           *           *           *           *
CCC GGT GTG TTG ACC ATC GCC GGC TGC CTC GCC GTC GAC GCT CAC GGT
GGG CCA CAC AAC TGG TAG CGG CCG ACG GAG CGG CAG CTG CGA GTG CCA
Pro Gly Val Leu Thr Ile Ala Gly Cys Leu Ala Val Asp Ala His Gly
                        AUTOTRANSLATION OF CO2

730         740         750         760         770
 *           *           *           *           *
GCA GCG CTC CCC GCC GAA GGC GAA GCA CAC GTT CCC GGA CAG ACT TTC
CGT CGC GAG GGG CGG CTT CCG CTT CGT GTG CAR GGG CCT GTC TGA ARG
Ala Ala Leu Pro Ala Glu Gly Glu Ala His Val Pro Gly Gln Thr Phe
                        AUTOTRANSLATION OF CO2

780         790         800         810
 *           *           *           *
GGC TCA CTC TCC AAC CTC GTC CAG GAG ACC TCC CTG ACC GCA GTG GTC TGG AAC
CCG AGT GAG AGG TTG GAG CAG GTC CTC TGG AGG GAC TGG CGT CAC CAG ACC TTG
Gly Ser Leu Ser Asn Leu Val Glu Gln Glu Thr Ser Leu Thr Ala Val Val Trp Asn
                        AUTOTRANSLATION OF CO2
```

```
820         830         840         850         860
 *           *           *           *           *
GGC AGT GAG TAC GCG CTC GAG ACG TAC GCG CGT AGC GAT GCA GCG ATC
CCG TCA CTC ATG CGC GAG CTC TGC ATG CGC GCA TCG CTA CGT CGC TAG
Gly Ser Glu Tyr Ala Leu Glu Thr Tyr Ala Arg Ser Asp Ala Ala Ile
                      AUTOTRANSLATION OF CO2

870         880         890         900
       *           *           *           *
AAG CCG CTG ACT CAC CTC GGA CGC ACC TTC CTC ACC GTG ACC
TTC GGC GAC GAC TGA GTG GAG CCT GCG TGG AAG GAG CAC TGG
Lys Pro Leu Thr His Leu Gly Arg Thr Phe Leu Thr Ser Val Thr
                      AUTOTRANSLATION OF CO2

920         930         940         950         960
 *           *           *           *           *
TTG CAG GCC GCT CCC AAC TAC CGC ATG CGC TGC GTC AGC CAC ACC GAC
AAC GTC CGG ACC CTT GAG TTG ATG GCG TAC CCG ACG TCG CAG TGG CTG
Leu Gln Ala Ala Pro Asn Tyr Arg Met Arg Cys Val Ser His Thr Asp
                      AUTOTRANSLATION OF CO2

970         980         990         1000        1010
       *           *           *           *           *
ATC GGT TGC CAG GAA CTC TTC GGC GCC CGG CGA CGC TCC GGA CGC ACC
TAG CCA ACC GTC CTT GAG AAG CCG CGG GCC GCT GCG AGG CCT GCG TGG
Ile Gly Trp Gln Glu Leu Phe Gly Ala Arg Gly His Arg Gly Ala Arg Thr
                      AUTOTRANSLATION OF CO2
```

FIG. 2E

```
        1020                 1030                 1040                 1050
          *                    *                    *                    *
*  *  o  o   o   o   o   o   o   o   o   o   o   o   o   o   o   o   o   o   o   o
TTC GAG AAG TTC GTC CGC GAA AAC GGT CGC GCA GAA GCA ATC TGG TAC
AAG CTC TTC AAG CAG GCG CTT TTG CCA GCG CGT CTT TAG ACC ATG
Phe Glu Lys Phe Val Arg Glu Asn Gly Arg Ala Glu Ala Ile Trp Tyr
                         AUTOTRANSLATION OF CO2

1060                 1070                 1080                 1090                 1100
          *                    *                    *                    *                    *
*  o  o   o   o   o   o   o   o   o   o   o   o   o   o   o   o   o   o   o   o
CCC TTC ACC GAA CGC CCG TGG ATG AAG GTG TGG TCA CTT GCC CCC ACC
GGG AAG TGG CTT GCG GGC ACC TAC TTC CAC ACC AGT GAA CGG GGG TGG
Pro Phe Thr Glu Arg Pro Trp Met Lys Val Trp Ser Leu Ala Pro Thr
                         AUTOTRANSLATION OF CO2

1110                 1120                 1130                 1140                 1150
          *                    *                    *                    *                    *
 o  o   o   o   o   o   o   o   o   o   o   o   o   o   o   o   o   o   o   o
AAG CGG CCG TTC TCG CGT GAG GTG ACC GGG CCC TAC AAC ATC TTC
TTC GCC GGC AAG AGC GCA CTC CAC CTG GGG CCC ATG TTG ATG TAG AAG
Lys Arg Pro Phe Ser Arg Glu Val Thr Gly Pro Tyr Asn Tyr Ile Phe
                         AUTOTRANSLATION OF CO2

1160                 1170                 1180                 1190                 1200
          *                    *                    *                    *                    *
*  o  o   o   o   o   o   o   o   o   o   o   o   o   o   o   o   o   o   o   o
TCC GAC AAC CTC CCG GAG CCG GAG CCC GAC ATG ATC GGG CAG ATC AAC
AGG CTG TTG GAG CTC GGC GGC CTC GGG CTG TAC TAG CCC GTC TAG TTG
Ser Asp Asn Leu Pro Glu Pro Val Thr Asp Met Ile Gly Gln Ile Asn
                         AUTOTRANSLATION OF CO2
```

EXPRESSION OF DNA SEQUENCES DERIVED FROM NOCARDIOFORM MICROORGANISMS

This is a continuation of application Ser. No. 07/914,048, filed Jul. 13, 1992, now abandoned, which is a continuation of application Ser. No. 07/436,234, filed Nov. 14, 1989, now abandoned, which is application is a Continuation-in-Part of application Ser. No. 07/269,669, filed Nov. 14, 1988, now abandoned.

BACKGROUND OF THE INVENTION

This invention relates to gene expression.

The organisms grouped as Nocardioforms in *Bergey's Manual of Systematic Bacteriology* (Williams and Wilkins, 1986, pp. 1458–1481) include nine genera which are close phylogenetically to Corynebacterium, Athrobacter and Mycobacterium. Members of the Nocardioforms including the genera Nocardia and Rhodococcus exhibit a wide range of useful metabolic activities including the assimilation of unusual compounds such as alkanes and aromatic hydrocarbons; the degradation of lignin, detergents and pesticides; the production of enzymes useful in xenobiotic transformations; and the biosynthesis of antibiotics, amino acids and biosurfactants. In particular, this group of bacteria have been exploited for their production of important steroid modifying enzymes, including cholesterol esterase and cholesterol oxidase, which are used in diagnostic assays to determine cholesterol levels in blood and serum.

The capacity to degrade cholesterol is widespread among microorganisms other than the Nocardioforms. For example, cholesterol oxidases have also been isolated from species of Mycobacterium, Pseudomonas, and Streptomyces. It is well known from scientific and patent literature and from commercial practice that the Nocardioform-type cholesterol oxidase is distinct from the other microbial cholesterol oxidases.

The Nocardioform enzyme is very stable and active over a wide pH range (pH 6.0–8.0), the Km for cholesterol is $1.4 \times 10^{-5}$ mol/liter at $25°$, and the enzyme is highly specific for $\Delta^4$- or $\Delta^5$-$3\beta$-sterols. As produced in the Nocardioforms, cholesterol oxidase is membrane associated and requires detergent extraction and lipid removal for purification.

Singer, et al., J. Bacteriol., 1988, Vol. 170, pp. 638–645, describes expression of genes in Rhodococcus sp. from both *E. coli* and Streptomyces sp. and the development of a shuttle plasmid based on an *E. coli* plasmid and containing a Rhodococcus plasmid-derived origin of replication. The plasmid is capable of replicating in *E. coli* and in several but not all of the Rhodococcus species tested.

SUMMARY OF THE INVENTION

We have discovered that recombinant DNA sequences derived from Nocardioform microorganisms can be expressed efficiently in a host microorganism.

The invention features, in one aspect, a cloning vector which expresses DNA sequences, derived from a Nocardioform organism, in a host microorganism. In preferred embodiments, the DNA sequence is derived from Rhodococcus sp. NCIB 10554 (National Collection of Industrial Bacteria, Aberdeen, Scotland); the DNA sequence encodes cholesterol oxidase; the organism in which the cloning vector can express the Nocardioform DNA is a gram-positive microorganism, more preferably a species of Streptomyces, and most preferably *S. lividans*; and the cloning vector is the plasmid pSL81.

Cholesterol oxidase is produced according to the invention by providing a cloning vector containing a DNA sequence encoding cholesterol oxidase, which is derived from a Nocardioform microorganism, transforming a host cell with the cloning vector to obtain a recombinant host cell, culturing the recombinant host cell under conditions permitting expression of the DNA sequence, and recovering the cholesterol oxidase. In preferred embodiments, the Nocardioform organism is Rhodococcus sp. NCIB 10554; the host cell is a gram-positive microorganism, preferably a species of Streptomyces, and more preferably *S. lividans*; and the cloning vector is the plasmid pSL81.

Cholesterol oxidase produced according to the invention can be used for determining cholesterol in a sample, by contacting the sample with the recombinant cholesterol oxidase and determining the extent of oxidation of cholesterol; specifically, by measuring oxygen consumption with an oxygen electrode; or by measuring the production of hydrogen peroxide; or by spectrophotometrically determining cholesterol conversion to $\Delta^4$-cholestenone.

The invention provides for the expression of DNA sequences derived from a Nocardioform microorganism in a host microorganism that is easier to manipulate under conditions of commercial production than is the parent organism itself, and for which cloning techniques are known. Recombinant cholesterol oxidase derived from Nocardioform microorganisms is expressed as an extracellular protein, an expression condition which can lead to substantially higher production of enzyme. Moreover, the expression does not require addition of an inducer, and the expressed enzyme is free of the lipids of the Nocardioform membrane.

Other features and advantages of the invention will be apparent from the following description of the preferred embodiment thereof, and from the claims.

BRIEF OF THE DRAWINGS

FIGS. 2A–2F are a sequence description of the Rhodococcus 10554 cholesterol oxidase gene.

DESCRIPTION OF THE PREFERRED EMBODIMENTS

Gene Isolation and Expression

Figure 1:
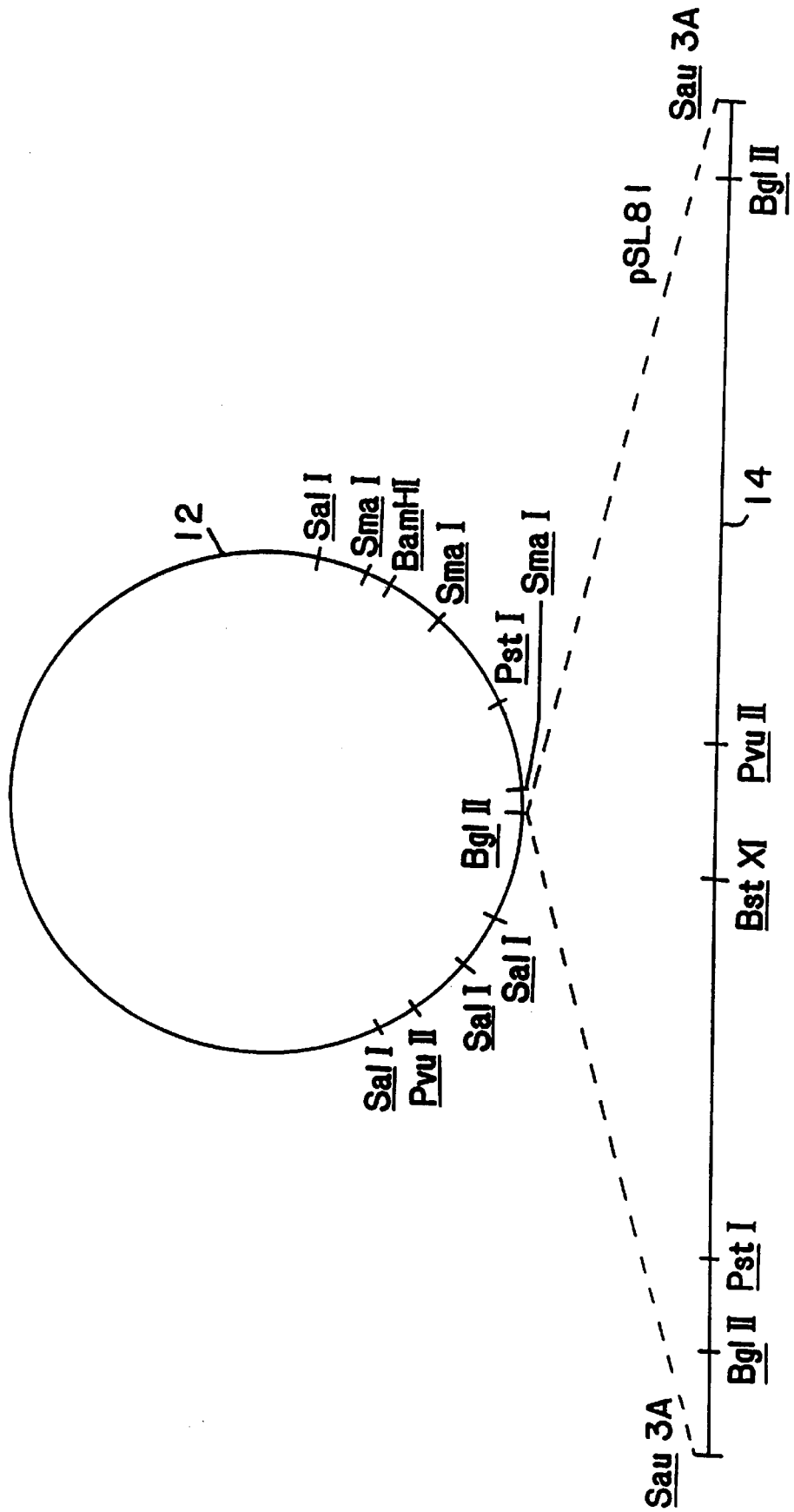
FIG. 1 is a restriction endonuclease map of plasmid pSL81.

The expression of DNA sequences derived from a Nocardioform microorganism can be accomplished, in general, by first constructing a genomic bank or library by incorporating the DNA sequences into a suitable cloning vector containing a suitable origin of replication compatible with the desired host organism. Next, a host cell from any microorganism, advantageously any gram-positive microorganism, such as, for example, species of Streptomyces or Bacillus, is transformed with the vector containing the DNA sequences. Then, transformants are screened for the activity of the desired gene product, and active clones are isolated and characterized.

Construction of Library

The following protocol, presented for illustrative purposes, describes construction of a genomic library of Rhodococcus sp. NCIB 10554 (Rhodococcus 10554) DNA in a host such as *S. lividans* which is capable of expressing the DNA from the parent microorganism. In the example described below, a population of transformed cells prepared using this library is screened for the expression of the cholesterol oxidase gene of Rhodococcus 10554.

Generally, a genomic library of Rhodococcus 10554 DNA was constructed from high molecular weight DNA which had been isolated and fragmented with the restriction enzyme Sau3A to yield fragments in the size range 4–8 kilobase pairs. Size fractionated DNA from Rhodococcus 10554 was then ligated to the cloning plasmid pIJ702 which had been digested with BglII. The pIJ702 plasmid is commercially available through the American Type Culture Collection (Rockville, Md., USA). Hybrid plasmids of the library were transformed into S. lividans cells to generate the genomic library of Rhodococcus 10554 DNA in the host microorganism.

Details of the procedure were as follows: A single colony of Rhodococcus 10554 was used to inoculate 50 ml of NBYE medium which contained per liter: Difco nutrient broth, 8 g, and Difco yeast extract, 5 g. Other appropriate media described for growing Rhodococcus sp. could also be used. The culture was grown for 48 hours at 30° C. and the cells collected by centrifugation at 10,000 rpm for 15 minutes in a Sorvall RC-5B centrifuge using an SS-34 rotor. The cells were resuspended in 18 ml of Tris-glucose (10 mM Tris-HCl, pH 8.0, 10 mM EDTA, 25% w/v glucose), and 2 ml of lysozyme solution (10 mg/ml lysozyme (Sigma) in Tris-glucose solution) was added. This mixture was incubated at 37° C. for 60 minutes. Next, 2.4 ml of 10% w/v sodium dodecyl sulfate (Sigma) was added and the mixture stirred vigorously to form a homogenous solution of lysed cells. The lysed cells were incubated at 55° C. for 2 hours, and then 2.7 ml of 5M NaClO$_4$ (Sigma) were added. Denatured protein and cell debris were removed by extracting the lysed cell solution twice with 20 ml chloroform:isoamyl alcohol (24:1) and resolving the phases by centrifugation at 12,000 rpm for 10 minutes in a Sorvall SS-34 rotor. The aqueous phase was removed and two volumes of cold ethanol added. The solution was mixed gently, and the high molecular weight DNA was collected using a glass rod as described by Marmur et al., 1961, J. Mol. Biol., Vol. 3, pp. 203–218. The collected DNA was washed twice in 70% ethanol and dissolved in 5 ml TE (10 mM Tris, 1 mM EDTA, pH 8.0). DNAse free RNAse (Sigma) was added at 100 mg/ml to the DNA solution and incubated at 42° C. for 30 minutes. Next, 0.6 ml of 10% w/v of sodium dodecyl sulfate and 0.6 ml of 5M NaCl were added, and the mixture was extracted once with phenol:chloroform (1:1) and once with chloroform:isoamyl alcohol (24:1). DNA was precipitated with 2 volumes of ethanol and collected as before using a glass rod. The DNA was washed once with 70% ethanol and air dried prior to resuspension in TE to a final concentration of approximately 1 mg/ml.

In order to establish the condition for isolating partially digested high molecular weight Rhodococcus 10554 DNA, test reactions were set up to digest DNA with different concentrations of Sau3A restriction enzyme. A reaction mixture was prepared with 10 µl DNA, 15 µl 10× Sau3A buffer (200 mM Tris HCl, pH 7.4, 50 mM MgCl$_2$, 500 mM KCl) and 125 µl water. Aliquots of 15µl were dispensed into tubes labeled 1–9 and chilled on ice. Exactly 4 units of Sau3A enzyme (10 units/µl BRL) were added to tube 1 and mixed well. Two-fold serial dilutions of the reaction mixtures from tube 1 sequentially through to tube 8 were performed to yield reaction mixtures containing two-fold decreasing concentrations of Sau3A enzyme. Tube 9 which contained no enzyme represented the undigested control reaction. The tubes were incubated at 37° C. for 1 hour and stopped by returning the tubes to ice and adding EDTA (20 mM). The extent of digestion in each tube was monitored by agarose gel electrophoresis, and the sample which yielded DNA fragments in the approximate range of 2–20 kb was scaled up 200 fold and the reaction repeated. The digested Rhodococcus 10554 DNA was separated by agarose gel electrophoresis using low gelling temperature agarose (SeaPlaque, FMC). The region of the gel containing DNA fragments in the size range 4–8 kb was excised with a sterile scalpel and the DNA recovered by electro-elution. The DNA was precipitated by conventional methods, and the precipitate was resuspended in TE to a concentration of 0.025 mg/ml.

A single colony of S. lividans/pIJ702 was used to inoculate 50 ml of YEME which contained per liter: Difco yeast extract, 3 g; Difco peptone, 5 g; Oxoid malt extract, 3 g; glucose, 10 g; sucrose, 340 g; MgCl$_2$ at 5 mM; and glycine at 0.4% w/v; and was supplemented with the plasmid selective agent thiostrepton (CalBiochem), at 50 µg/ml. Other media described for Streptomyces could also be used. The culture was incubated at 30° C. for 3 days. The cells were harvested by centrifugation at 10,000 rpm for 30 minutes using a Sorvall centrifuge and SS-34 rotor. The pellet was resuspended in 5 ml TSE Buffer (25 mM Tris, pH 8.0; 0.3M sucrose; 25 mM EDTA) containing 10 mg lysozyme. The cells were incubated at 37° C. for 30 minutes. A 3 ml volume of alkaline SDS solution (0.3M NaOH, 2% w/v sodium dodecyl sulfate) was added, and the mixture was incubated at room temperature for 10 minutes and at 70° C. for 10 minutes. The lysed cell solution was cooled to room temperature and extracted with 1 volume of phenol: chloroform (1:1). The aqueous phase was removed to a clean tube and 0.3M sodium acetate, pH 4.8, and 1 volume of isopropanol added. The DNA was precipitated for 30 minutes at −20° C. and recovered by centrifugation, using a Sorvall SS-34 rotor at 10,000 rpm for 10 minutes. The pellet was resuspended in 2 ml TE and the plasmid DNA purified by ultracentrifugation to equilibrium in a cesium chloride density gradient according to known techniques.

Plasmid pIJ702 prepared as above was resuspended in TE to a concentration of 1 mg/ml. About 10 µl (10 µg) of DNA was added to 5 µl 10× BglII buffer (500 mM Tris HCl, pH 7.4; 50 mM MgCl$_2$; 500 mM KCl), 32 µl distilled water and 3 µl of BglII restriction enzyme (10 units/µl, BRL) and incubated for 2 hours at 37° C. The reaction was terminated by one extraction with phenol:chloroform (1:1) and one extraction with chloroform:isoamyl alcohol (24:1). The DNA was precipitated by the addition of one-half volume of 7.5M ammonium acetate and 2 volumes of cold ethanol. After incubation at −20° C. for at least 2 hours, the DNA was collected in an Eppendorf microfuge by centrifugation for 10 minutes. The DNA pellet was washed once with 70% ethanol, dried and resuspended in 50 µl 10 mM Tris HCl, pH 8.0. To dephosphorylate the D A, 1 µl of calf intestine alkaline phosphatase (2 U/µl, IBI) was added and the reaction incubated at 37° C. for 30 minutes. The reaction was stopped by adding 150 µl stop buffer (10 mM Tris HCl, pH 7.5; 1 mM EDTA, pH 7.5; 200 mM NaCl; 0.5% w/v sodium dodecyl sulfate) and then extracted once with phenol:chloroform (1:1) and once with chloroform:isoamyl alcohol (24:1). The DNA was precipitated with ethanol, dried and resuspended in TE to a final concentration of 0.05 mg/ml and stored at −20° C.

About 10 µl (0.5 µg) of the dephosphorylated BqlII digested pIJ702 DNA was added to about 20 µl (0.5 µg) of the Sau3A digested Rhodococcus DNA. A 20 µl aliquot of 5× ligase buffer (BRL), 0.5 µl ligase (NEB) and 50 µl water were added and the ligation reaction incubated at 14° C. for 20 hours. The reaction was terminated by heating the mixture to 65° C. for 10 minutes, and the sample was stored at −20° C.

A vegetative inoculum was prepared by growing *S. lividans* in 25 ml culture broth as described for the preparation of *S. lividans*/pIJ702, except the medium contained no thiostrepton. The cells were harvested in a benchtop centrifuge at 3,000 rpm for 10 minutes and washed twice with 10 ml of 10.3% w/v sucrose. The cell pellet was resuspended in 4 ml lysozyme medium (L-medium, Thompson et al., 1982, J. Bacteriol., Vol. 151, pp. 668–677) and incubated at 30° C. for 30 minutes. A 5 ml aliquot of protoplast medium (P-medium, Okanishi, et al., 1974, J. Gen. Microbiol., Vil. 80, pp. 389–400) was added and the solution mixed by pipetting up and down. Protoplasts were filtered through glass wool (which traps mycelia but allows protoplasts to pass through) harvested by centrifugation, and resuspended in 2 ml P-medium. Protoplasts were used fresh or stored frozen in P-medium at −70° C.

Up to 3 µl of ligated plasmid DNA in ligation buffer was mixed gently with 50 µl *S. lividans* protoplasts in a small sterile tube. To this mixture, 200 µl transformation buffer (T-buffer, Thompson, et al., 1982, J. Bacteriol., Vol. 151, pp. 668–667) was added and pipetted to mix. Immediately, the cells were spread gently onto R2YE medium (Thompson, et al., 1980, Nature (London), Vol. 286, pp. 525–527) and incubated overnight at 30° C. The regenerated protoplasts were overlaid with filter paper (Whatman 541, 9.0 cm) containing 100 µg/ml thiostrepton and incubated at 30° C. for 3 days. About 200–500 transformants per plate were obtained using these transformation conditions. Approximately 12,000 thiostrepton-resistant *S. lividans* transformants were obtained in this way. Over 70% of these transformants contained recombinant pIJ702 plasmids as estimated by miniprep DNA analysis. These recombinant plasmids represented the genomic library of Rhodococcus 10554 DNA.

Screening for Cholesterol Oxidase Activity

As an example, showing the expression of one DNA sequence derived from a Nocardioform microorganism, recombinant *S. lividans* cells containing the genomic library of Rhodococcus 10554 DNA were screened for the expression of cholesterol oxidase activity. Cholesterol oxidase was determined using a modified method of Allain et al., 1974, Physical Chem., Vol. 20, pp. 470–475. Filter paper discs were soaked in an assay buffer containing 4-aminoantipyrine, phenol, horse radish peroxidase and triton-X100, and laid down on colonies growing on agar medium containing cholesterol substrate. Alternatively, these colonies could be assayed by halo formation on agar medium containing cholesterol, in which halo formation depended on the conversion of cholesterol to cholestenone by soluble cholesterol oxidase. Recombinant *S. lividans* colonies which produced cholesterol oxidase were purified, and characterized.

Details of the screening of the genomic library for cholesterol oxidase activity were as follows: Filter papers used to apply thiostrepton drug to R2YE transformation plates for the selection of *S. lividans* transformants, were lifted and placed onto screening plates [medium containing per liter: agar, 15 g; glycerol, 20 g; yeast extract, 1 g; $MgSO_4$, 0.66 g; buffer salts, 66 ml (per liter: $Na_2HPO_4$, 28 g; $NaH_2PO_4$, 30 g; $K_2HPO_4$, 20 g; $(NH_4)_2SO_4$, 127.5 g) and trace salts, 2 ml (per liter: concentrated HCl, 250 ml; $CaCl_2$, 3.57 g; $ZnSO_4$, 20 g; $CuCl_2$, 0.85 g; $NaMoO_4$, 4.8 g; $MnCl_2$, 2.0 g; $FeCl_3$, 5.4 g; boric acid, 0.3 g; $CoCl_2$, 2.4 g)] with cholesterol (1.6 mM, Sigma) and thiostrepton (50 µg/ml). These replica plates were incubated at 30° C. for 3 days. The replica filters were removed and replaced with sterile filter paper discs soaked in cholesterol oxidase assay reagent (100 mM citric acid buffer, pH 6.0; 0.2 mM 4-aminoantipyrine (Aldrich); horse radish peroxidase I, 600 units per liter; 6.4 mM cholesterol; 10 mM phenol and 4% w/v Tritonx100). The plates were incubated at 30° C., and the colonies were screened over a 4 hour period for the development of a red zone due to cholesterol oxidase activity which diffused onto the white filter paper. After incubation at 30° C. for 4 hours, the assay reagent filter papers were removed from the screening plates, and the plates were re-incubated at 30° C. overnight to allow for the formation of clear halos associated with cholesterol oxidase degradation of cholesterol. From the approximately 8,000 recombinant *S. lividans* colonies screened, two showed cholesterol oxidase activity. The plasmid DNA from one of these isolates was called pSL81 and was analyzed further.

Plasmid DNA from the *S. lividans*/pSL81 recombinant was isolated and transformed back into *S. lividans* using the same procedure described for isolating and transforming pIJ702. All the thiostrepton-resistant transformants obtained contained the same plasmid pIJ702 with approximately 6 kb insert DNA, and showed the cholesterol oxidase activity diagnostic of the original recombinant. Curing of plasmid pSL81 from *S. lividans* cells by growth in the absence of drug selective pressure resulted in the simultaneous loss of thiostrepton resistance and cholesterol oxidase activity. Southern hybridization demonstrated that the insert DNA was derived from the Rhodococcus 10554 genome. Referring to FIG. 1, the recombinant plasmid designated pSL81 includes cloning vector pIJ702 12 and insert DNA 14 from Rhodococcus 10554, and has restriction endonuclease sites as indicated.

Plasmid pSL81, prepared as above, was used to probe chromosomal digests from the cholesterol oxidase producing Nocardioforms Rhodococcus NCIB 10554, *R. erythropolis* NCIB 9158, *Nocardia erythropolis* ATCC 17895 and *Nocardia erythropolis* ATCC 4277. The strains all showed cross-hybridizing DNA bands suggesting that the cholesterol oxidase coding region in these Nocardioforms is the same. Plasmid pSL81 showed no specific cross hybridization with DNA isolated from a cholesterol oxidase producing Streptomyces, namely *Streptomyces violascene* NRRL B-2700.

DNA Sequencing

Figure 3:
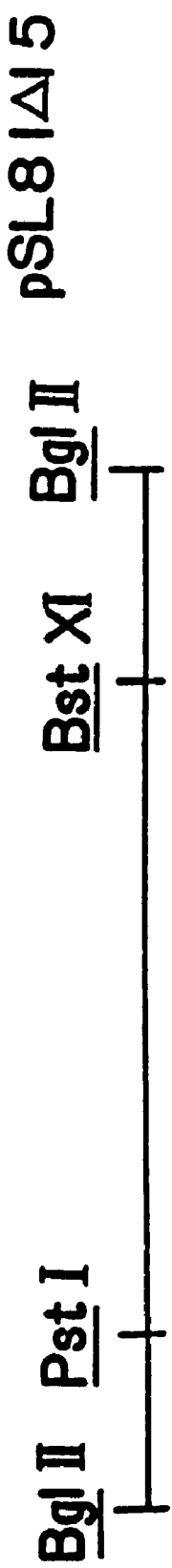
FIG. 3 is a restriction endonuclease map of plasmid pSL81, showing the position of the pSL81Δ15 fragment.

In order to sequence the cholesterol oxidase gene, subclones of pSL81 were constructed and a cholesterol oxidase coding region was localized to a 2.8 kb BglII fragment in the subclone pSL81Δ15 (FIG. 3). This fragment was then introduced into *E. coli* on plasmid pBR322, and a series of deletion derivatives were constructed using available restriction sites. Sequencing was performed on denatured double stranded plasmid DNA using the dideoxy chain termination method of Sanger et al., PNAS USA, Vol. 74, pp. 5463–67. Specifically, a Sequenase Version 2.0 kit (United States Biochemical Corp.) was used according to the manufacturer's specifications. Deoxyguanidine triphosphate or Deoxy-7-deazoguanidine triphosphate was used to terminate chain polymerization reactions depending on the degree of G+C content of a particular region of DNA being sequenced. The primer extended oligonucleotides were electrophoresed on denaturing 6% polyacrylamide and the DNA sequences of adjacent DNA fragments were pieced together to construct a complete DNA sequence of the cholesterol oxidase gene. The sequence is shown in FIG. 2.

Subcloning of the Rhodococcus cholesterol oxidase gene in pSL81Δ15 can result in an increase in expression of the cholesterol oxidase protein. Recombinant *S. lividans* cells were grown on RZYE agar containing 50 µg/ml thiostrepton. After 2–3 days incubation at 30° C., the mycelia and spores were scraped from the surface of the agar and used to inoculate 50 ml YEME+12.5 µg/ml thiostrepton seed cultures. These cultures were grown at 30° C. with vigorous shaking and after 48 h, 2 l fermenters containing YEME+ 12.5 µg/ml thiostrepton were inoculated with the seed. The fermentations were controlled at 28° C. and pH 7.0 with aeration at 0.5 l/min and agitation at 1000 rpm. Cholesterol oxidase activity peaked after 48 h and in some such cultures expression was substantially greater in the *S. lividans/*pSL81Δ15 fermentations than in the *S. lividans*/pSL81 fermentations.

Protein Characterization

Recombinant cholesterol oxidase was isolated from 3 day old cultures of *S. lividans*/pSL81 cells grown in YEME (25 ml) containing thiostrepton (50 µg/ml). Non-recombinant cholesterol oxidase was isolated from 48 hour Rhodococcus 10554 cultures grown in liquid production medium which was the same medium as that used for the screening plates not solidified with agar. Induction experiments were performed using the same growth conditions in the presence of sterols as an inducer. Intracellular and extracellular fractions were recovered by centrifugation and assayed for cholesterol oxidase activity using a cholesterol oxidase specific diagnostic assay. The specificity of the recombinant cholesterol oxidase from *S. lividans* and the purified cholesterol oxidase from Rhodococcus 10554 were compared using various sterols substrates. Both enzymes showed similar profiles with the order of activity being cholesterol, pregnenolone, dihydroxycholesterol, stigmasterol and ergosterol.

Recombinant cholesterol oxidase from *S. lividans*/pSL81 was functional in standard diagnostic assays for the determination of cholesterol. An aliquot of cell-free supernatant from a 3 day old culture of YEME grown recombinant cells was mixed with the cholesterol oxidase assay reagent (1.4 ml of 0.33 mg/ml 4-aminophenazone in 0.1M phosphate buffer, pH 7.0, 0.05% Triton X-100 (w/v); 1.4 ml of 1 mg/ml phenol in phosphate-Triton X buffer; 0.1 ml of 4 mM cholesterol; and 0.01 ml of 10 mg/ml peroxidase) and incubated at 30° C. Hydrogen peroxide formed during the oxidation of cholesterol and chelated with the aminoantipyrine in the assay mixture was determined by measuring the absorption of the red complex at 505 nm versus a reagent blank containing water. The rate of cholesterol degradation by the recombinant enzyme was also measured directly by following the increase in absorbance at 240 nm owing to $\Delta^4$-cholestenone production. To 2.9 ml of sodium phosphate buffer (0.1M, pH 7.0) in a cuvette, 100 µl of 3% Triton X-100 (w/v) and 50 µl of a 6 mM cholesterol solution were added. Diluted enzyme at approximately 0.2 U/ml in buffer was added and the absorbance at 240 nm monitored using a Beckman spectrophotometer. Cholesterol oxidase activity was calculated as:

$$\text{units/mg} = \frac{OD/\min \times RV}{12.3 \times DF \times SV \times PC \ (\text{mg/ml})},$$

where
RV=reaction volume
DF=dilution factor
SV=sample volume
PC=protein concentration Further characterization of the recombinant cholesterol oxidase from *S. lividans*/pSL81 demonstrated that the enzyme could also be used to determine cholesterol in sera using the peroxidase coupled reaction.

Recombinant cholesterol oxidase from *S. livldans*/pSL81 and purified Rhodococcus 10554 cholesterol oxidase were analyzed by polyacrylamide gel electrophoresis using a 10% polyacrylamide gel and the buffer system of Laemelli, 1970, Nature, Vol. 227, pp. 680 et seq. Both enzymes were determined to be approximately 55 kD in size when compared with Biorad molecular weight standards.

Peptide Sequencing

Recombinant cholesterol oxidase from *S. lividans/* pSL8115 and non-recombinant cholesterol oxidase from *R. rhodococcus* were isolated as single bands from a polyacrylamide gel, and the amino-terminal peptide sequences were determined using a protein sequenator. Two peptide sequences were recovered from the recombinant protein band:

$NH_2$-Gly-Gly-Pro-Val-Ser-Thr-Leu-Thr-Pro-Pro-Pro-Ala-Phe-, and $NH_2$-Gly-Pro-Val-Ser-Thr-Leu-Thr-Pro-Pro-Pro-Ala-Phe-.

These peptide sequences are identical to those deduced directly from the DNA sequence between positions 280 and 320, and between positions 283 and 320, respectively. The elimination of a glycine residue at the N-terminus of one recombinant sequence is probably owing to a difference in post-translational processing by the host cell.

Amino terminal sequencing of cholesterol oxidase from *R. rhodococcus* identified the sequence $NH_2$-Thr-Pro-Pro-Pro-Ala-Phe-Pro-Glu-Gly-Ile-Ala-Leu-Tyr-Gln-Gln-, which corresponds to the peptide sequence deduced from the DNA sequence between positions 300 and 346. Therefore, the enzyme found in the *S. lividans*/pSL81Δ15 culture medium is either 6 or 7 amino acids longer that the membrane bound enzyme found in *R. rhodococcus*.

Processing of gram-positive secreted proteins often involves signal sequence cleavage followed by hydrolysis at a secondary processing site. In the case of native cholesterol oxidase this secondary site is at the threonine. Apparently such a secondary cleavage does not occur when the protein is synthesized and secreted extracellularly by *S. lividans*.

OTHER EMBODIMENTS

Other embodiments are within the following claims. For example, other species of any genus of the Nocardioforms including Rhodococcus NCIB 10554, *R. erythropolis* NCIB 9158, *Nocardia erythropolis* ATCC 17895 and *Nocardia erythropolis* ATCC 4277 could be used to prepare the genomic library; or the libraries could be screened for other useful metabolic activities such as the assimilation of alkanes and aromatic hydrocarbons; the degradation of lignin, detergents, and pesticides; the production of enzymes useful in xenobiotic transformation; the biosynthesis of antibiotics, amino acids and biosurfactants; and the production of other steroid modifying enzymes such as cholesterol esterase.

As other Streptomyces and also Bacillus species share the advantages of *S. lividans* for the expression of heterologous genes, they could also serve as suitable hosts for the expression of DNA sequences derived from Nocardioform microorganisms. Other bacteria belonging to the high G+C subdivision of the gram-positive bacteria including any of the Nocardioforms, Mycobacterium, Corynebacterium, and Athrobacter would be suitable hosts for cloning DNA sequences derived from Nocardioform microorganisms.

*S. lividans*/pSL81 can undergo rearrangement in one or more regions outside the cholesterol oxidase coding region and can retain cholesterol oxidase transforming activity. One such S. lividans/pSL81 rearranged plasmid, has at least 3.6 kb of the 6 kb Rhodococcus DNA unchanged as determined by restriction mapping. In this rearranged S. lividans/pSL81 plasmid a DNA insertion of approximately 2.5 kb has occurred in the region to the right of the PvuII site. Cholesterol oxidase was recoverable from cultures of S. lividans transformed with this rearranged plasmid, in lower quantities than from S. lividans/pSL81 cultures.

In still other embodiments expression of cholesterol oxidase may be increased by further manipulating the pSL81Δ15 clone, as will be apparent to one skilled in the art. For example, a higher copy number vector could be used, such as, for example, pIJ303, described in Hopwood et al., 1985, *Genetic Manipulation of Streptomyces: A Laboratory Manual*. Gene expression could also be enhanced by replacing the cholesterol oxidase promoter with a stronger exogenous promoters, such as ErmE promoter, described in Bibb et al., 1985, Gene, Vol. 38, pp. 215–226; aph promoter, described in Hopwood et al., 1985; or a tac promoter, described in Amman et al., 1984, Gene, Vol. 25, pp. 167 et seq.

DEPOSIT

Under the terms of the Budapest Treaty on the International Recognition of the Deposit of Microorganisms for the Purpose of Patent Procedure, deposit of plasmid pSL81 has been made with the American Type Culture Collection (ATCC) of Rockville, Md., USA, where the deposit was given Accession Number 67853, deposited Nov. 9, 1988.

Applicants' assignee, Genzyme Corporation, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. § 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

What is claimed is:

1. A cloning vector comprising DNA sequence isolated from a Rhodococcus microorganism, said DNA sequence encoding cholesterol oxidase, and said cloning vector expressing said DNA sequence in a host Streptomyces microorganism, said cloning vector being plasmid pSL81.

2. The cloning vector of claim 1 wherein said Rhodococcus microorganism is Rhodococcus sp. NCIB 10554.

3. The cloning vector of claim 1 wherein said host microorganism is S. lividans.

4. The cloning vector of claim 1 which is plasmid pSL81.

5. A Streptomyces cell transformed with the cloning vector of claim 1.

6. S.lividans cell transformed with the cloning vector of claim 1.

7. A method for expressing a DNA sequence encoding cholesterol oxidase isolated from a Nocardioform microorganism selected from the group consisting of Rhodococcus sp. NCIB 10554, *R. erythropolis* NCIB 9158, *Nocardia erythropolis* ATCC 17895, and *Nocardia erythropolis* ATCC 4277, comprising transforming a host S. lividans cell with a cloning vector containing said DNA sequence to obtain a recombinant cell, and culturing said recombinant cell under conditions permitting expression of said DNA sequence as an extracellular protein which is not membrane associated.

8. A method for producing cholesterol oxidase comprising providing a cloning vector containing a DNA sequence derived from a Nocardioform microorganism selected from the group consisting of Rhodococcus sp. NCIB 10554, *R. erythropolis* NCIB 9158, *Nocardia erythropolis* ATCC 17895, and *Nocardia erythronolis* ATCC 4277, said DNA sequence encoding cholesterol oxidase, transforming a host S. lividans cell with said cloning vector to obtain a recombinant host cell, culturing said recombinant host cell under conditions permitting expression of said DNA sequence as an extracellular protein which is not membrane associated, and recovering the cholesterol oxidase.

9. The method of claim 8 wherein said cloning vector is plasmid pSL81.

10. The cloning vector of claim 1, wherein said DNA sequence encodes an amino acid sequence comprising the sequence:

Thr Pro Pro Pro Ala Phe Pro Glu Gly Ile Ala Leu Tyr Gln Gln.

11. The cloning vector of claim 10, wherein said DNA sequence encodes an amino acid sequence comprising the sequence:

Gly Pro Val Ser Thr Leu Thr Pro Pro Pro Ala Phe Pro Glu Gly Ile Ala Leu Tyr Gln Gln.

12. The cloning vector of claim 11, wherein said DNA sequence encodes an amino acid sequence comprising the sequence:

Gly Gly Pro Val Ser Thr Leu Thr Pro Pro Pro Ala Phe Pro Glu Gly Ile Ala Leu Tyr Gln Gln.

13. The cloning vector of claim 12, wherein said DNA sequence encodes an amino acid sequence comprising the sequence:

Met Thr Ala Gln Asp Glu Lys Phe Arg Leu Ser Arg Arg Gly Phe Met Ala Ala Gly Ala Gly Ala Val Ala Ala Thr Ala Phe Ala Gly Trp Thr Pro Ala Tyr Ala Val Pro Ala Gly Ser Ser Gly Ser Ala Gly Gly Pro Val Ser Thr Leu Thr Pro Pro Pro Ala Phe Pro Glu Gly Ile Ala Leu Tyr Gln Gln Ala Tyr Gln Asn Trp Ser Lys Glu Ile Met Leu Asp.

14. The cloning vector of claim 1, wherein said DNA sequence comprises the sequence:

ACA CCG CCG CCC GCC TTC CCC GAA GGC ATC GCG CTG TAC CAG CAG.

15. The cloning vector of claim 14, wherein said DNA sequence comprises the sequence:

GGT CCT GTC TCC ACC CTC ACA CCG CCG CCC GCC TTC CCC GAA GGC ATC GCG CTG TAC CAG CAG.

16. The cloning vector of claim 15, wherein said DNA sequence comprises the sequence:

GGT GGT CCT GTC TCC ACC CTC ACA CCG CCG CCC GCC TTC CCC GAA GGC ATC GCG CTG TAC CAG CAG.

17. The cloning vector of claim 16, wherein said DNA sequence comprises the sequence:

CGAAG ATG ACG GCA CAA GAC GAA AAG TTC CGA CTG TCC CGA CGA GGT TTC ATG GCC GCT GGA GCC GGC GCC GTG GCA GCG ACC GCA TTC GCC GGC TGG ACG CCG GCC TAC GCC

GTC CCC GCC GGC TCC TCC GGC TCC GCG
GGT GGT CCT GTC TCC ACC CTC ACA CCG CCG
CCC GCC TTC CCC GAA GGC ATC GCG CTG TAC
CAG CAG GCA TAT CAG AAC TGG TCC AAA
GAG ATC ATG CTC GAC.

18. The cloning vector of claim 17, wherein said DNA sequence comprises the sequence:

GGGACTCCTG ATCTCAGCTT CCGTACTGGA
GCGCGAAGCT CCTGCCCTGG CTGACGTAGT
TCTCACTCTT GTCTGATACC AACCTGTCTG
ATACCCACCT GTTAGAACTC ACCGTAGTTC
TCGAACCCGA TGGAGTAGCC CGAAG ATG ACG
GCA CAA GAC GAA AAG TTC CGA CTG TCC
CGA CGA GGT TTC ATG GCC GCT GGA GCC
GGC GCC GTG GCA GCG ACC GCA TTC GCC
GGC TGG ACG CCG GCC TAC GCC GTC CCC
GCC GGC TCG TCC GGC TCC GCG GGT GGT
CCT GTC TCC ACC CTC ACA CCG CCG CCC GCC
TTC CCC GAA GGC ATC GCG CTG TAC CAG CAG
GCA TAT CAG AAC TGG TCC AAA GAG ATC ATG
CTC GAC.

19. The vector of claim 1, further comprising an ErmE promoter.

20. The vector of claim 1, further comprising an aph promoter.

21. The vector of claim 1, further comprising a tac promoter.

\* \* \* \* \*